(12) United States Patent
Wingeier et al.

(10) Patent No.: US 11,400,290 B2
(45) Date of Patent: *Aug. 2, 2022

(54) METHOD AND SYSTEM FOR IMPROVING PROVISION OF ELECTRICAL STIMULATION

(71) Applicant: Flow Neuroscience, Inc., Palo Alto, CA (US)

(72) Inventors: Brett Wingeier, San Francisco, CA (US); Shawn Razek, San Francisco, CA (US); Kevin G. Babcock, San Francisco, CA (US); Alan Fineberg, San Francisco, CA (US); Rich Lowenberg, San Francisco, CA (US); Patrick Wolber, San Francisco, CA (US)

(73) Assignee: Flow Neuroscience, Inc., Palo Alto, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/391,569

(22) Filed: Apr. 23, 2019

(65) Prior Publication Data

US 2019/0247655 A1      Aug. 15, 2019

Related U.S. Application Data

(63) Continuation of application No. 15/426,212, filed on Feb. 7, 2017, now Pat. No. 10,315,033.

(Continued)

(51) Int. Cl.
*A61N 1/36*  (2006.01)
*A61N 1/04*  (2006.01)
*A61N 1/08*  (2006.01)

(52) U.S. Cl.
CPC ....... *A61N 1/36025* (2013.01); *A61N 1/0456* (2013.01); *A61N 1/0472* (2013.01);
(Continued)

(58) Field of Classification Search
CPC ....... A61N 1/0456; A61N 1/0472; A61N 1/08
See application file for complete search history.

(56) References Cited

U.S. PATENT DOCUMENTS 3,472,233 A    10/1969  Sarbacher
4,928,696 A     5/1990  Henderson et al.
(Continued)

FOREIGN PATENT DOCUMENTS

CN       103517732 A         1/2014
DE    102010052710 A1 *    5/2012   ............. A61B 5/053
(Continued)

OTHER PUBLICATIONS

US 8,919,831 B2, 12/2014, Tateishi et al. (withdrawn)

*Primary Examiner* — Joseph M Dietrich
(74) *Attorney, Agent, or Firm* — Jeffrey Schox; Caitlin Ploch

(57) ABSTRACT

A method and system for providing stimulation to a user, the method including: transitioning a stimulation device from a baseline state to a first impedance monitoring state; during the first impedance monitoring state, guiding, an adjustment of a position of the stimulation device at a head region of the user to satisfy a first impedance criterion; upon satisfaction of the first impedance criterion, transitioning the stimulation device from the first impedance monitoring state to a stimulation regime that comprises a second monitoring state having a second criterion; upon detection of failure to satisfy the second criterion, transitioning the stimulation device from the stimulation regime to the first impedance monitoring state; and upon detecting that a third impedance criterion (Continued)

of the first impedance monitoring state is satisfied, transitioning the stimulation device from the first impedance monitoring state to the stimulation regime.

20 Claims, 7 Drawing Sheets

Related U.S. Application Data

(60) Provisional application No. 62/292,511, filed on Feb. 8, 2016, provisional application No. 62/442,350, filed on Jan. 4, 2017.

(52) U.S. Cl.
CPC ............ *A61N 1/08* (2013.01); *A61N 1/36031* (2017.08); *A61N 1/36034* (2017.08); *A61N 2001/083* (2013.01)

(56) References Cited

U.S. PATENT DOCUMENTS

| | | |
|---|---|---|
| 4,967,038 A | 10/1990 | Gevins et al. |
| 4,977,895 A | 12/1990 | Tannenbaum |
| 5,058,605 A | 10/1991 | Slovak |
| 5,087,242 A | 2/1992 | Petelenz et al. |
| 5,137,817 A | 8/1992 | Busta et al. |
| 5,250,023 A | 10/1993 | Lee et al. |
| 5,387,231 A | 2/1995 | Sporer |
| 5,622,168 A | 4/1997 | Keusch et al. |
| 6,077,237 A | 6/2000 | Campbell et al. |
| 6,263,226 B1 | 7/2001 | Axelgaard et al. |
| 6,379,324 B1 | 4/2002 | Gartstein et al. |
| 6,406,811 B1 | 6/2002 | Hall et al. |
| 6,480,743 B1 | 11/2002 | Kirkpatrick et al. |
| 6,505,079 B1 | 1/2003 | Foster et al. |
| 6,510,333 B1 | 1/2003 | Licata et al. |
| 7,024,247 B2 | 4/2006 | Gliner et al. |
| 7,551,952 B2 | 6/2009 | Gevins et al. |
| 7,610,095 B2 | 10/2009 | Naisberg |
| 7,813,802 B2 | 10/2010 | Tcheng et al. |
| 7,818,515 B1 | 10/2010 | Umbehocker et al. |
| 7,828,947 B2 | 11/2010 | Oki et al. |
| 7,877,146 B2 | 1/2011 | Ansarinia et al. |
| 7,894,905 B2 | 2/2011 | John et al. |
| 7,966,073 B2 | 6/2011 | Pless et al. |
| 7,988,917 B2 | 8/2011 | Roesicke et al. |
| 8,116,875 B2 | 2/2012 | Osypka et al. |
| 8,121,694 B2 | 2/2012 | Molnar et al. |
| 8,195,174 B2 | 6/2012 | Lee et al. |
| 8,239,030 B1 | 8/2012 | Hagedorn et al. |
| 8,290,596 B2 | 10/2012 | Wei et al. |
| 8,301,265 B2 | 10/2012 | Starkebaum |
| 8,349,554 B2 | 1/2013 | Bahrami et al. |
| 8,380,316 B2 | 2/2013 | Hagedorn et al. |
| 8,419,716 B2 | 4/2013 | Weissenrieder-Norlin et al. |
| 8,473,063 B2 | 6/2013 | Gupta et al. |
| 8,554,324 B2 | 10/2013 | Brocke |
| 8,583,237 B2 | 11/2013 | Bedenbaugh |
| 8,591,392 B2 | 11/2013 | Bentwich et al. |
| 8,626,259 B2 | 1/2014 | Besio |
| 8,706,181 B2 | 4/2014 | Stypulkowski et al. |
| 8,795,174 B2 | 8/2014 | Manicka et al. |
| 8,818,515 B2 | 8/2014 | Bikson et al. |
| 8,838,247 B2 | 9/2014 | Hagedorn et al. |
| 8,874,220 B2 | 10/2014 | Draghici et al. |
| 8,874,227 B2 | 10/2014 | Simon et al. |
| 8,880,173 B2 | 11/2014 | Diubaldi et al. |
| 8,903,494 B2 | 12/2014 | Goldwasser et al. |
| 8,938,301 B2 | 1/2015 | Hagedorn |
| 8,979,837 B2 | 3/2015 | De La Rama et al. |
| 8,989,863 B2 | 3/2015 | Osorio |
| 9,002,458 B2 | 4/2015 | Pal et al. |
| 9,080,918 B2 | 7/2015 | Fishel et al. |
| 9,186,505 B2 | 11/2015 | Katsnelson |
| 9,393,430 B2 | 7/2016 | Demers et al. |
| 9,399,126 B2 | 7/2016 | Pal et al. |
| 9,433,774 B2 | 9/2016 | Dar et al. |
| 9,440,063 B2 | 9/2016 | Ho et al. |
| 9,440,070 B2 | 9/2016 | Goldwasser et al. |
| 9,486,618 B2 | 11/2016 | Wingeier et al. |
| 9,517,345 B2 | 12/2016 | Meffin et al. |
| 9,630,005 B2 | 4/2017 | Wingeier et al. |
| 9,643,001 B2 | 5/2017 | Wu et al. |
| 9,731,127 B2 | 8/2017 | Kealey et al. |
| 9,757,561 B2 | 9/2017 | Wingeier et al. |
| 9,770,204 B2 | 9/2017 | Wu et al. |
| 9,782,585 B2 | 10/2017 | Wingeier |
| 9,802,042 B2 | 10/2017 | Wingeier et al. |
| 9,877,664 B2 | 1/2018 | Machon et al. |
| 9,889,290 B2 | 2/2018 | Wingeier et al. |
| 9,913,973 B2 | 3/2018 | Yanaki |
| 9,981,128 B2 | 5/2018 | Wingeier |
| 10,238,870 B2 | 3/2019 | Pilly et al. |
| 2002/0169485 A1 | 11/2002 | Pless et al. |
| 2004/0019370 A1 | 1/2004 | Gliner et al. |
| 2005/0165460 A1 | 7/2005 | Erfan |
| 2006/0111754 A1 | 5/2006 | Ansarinia et al. |
| 2006/0212093 A1 | 9/2006 | Pless et al. |
| 2006/0229502 A1 | 10/2006 | Pollock et al. |
| 2006/0259094 A1 | 11/2006 | Grinshpoon et al. |
| 2007/0015984 A1 | 1/2007 | Yeo et al. |
| 2007/0023779 A1 | 2/2007 | Hirose et al. |
| 2007/0027498 A1 | 2/2007 | Maschino et al. |
| 2007/0038265 A1 | 2/2007 | Tcheng et al. |
| 2007/0093706 A1 | 4/2007 | Gevins et al. |
| 2007/0118070 A1 | 5/2007 | Cormier et al. |
| 2007/0213783 A1 | 9/2007 | Pless |
| 2007/0237678 A1 | 10/2007 | Roesicke et al. |
| 2007/0237797 A1 | 10/2007 | Peyman |
| 2007/0238945 A1 | 10/2007 | Delic et al. |
| 2007/0250145 A1 | 10/2007 | Kraus et al. |
| 2008/0004676 A1 | 1/2008 | Osypka et al. |
| 2008/0021520 A1 | 1/2008 | Dietrich |
| 2008/0027345 A1 | 1/2008 | Kumada et al. |
| 2009/0069803 A1 | 3/2009 | Starkebaum |
| 2009/0099627 A1 | 4/2009 | Molnar et al. |
| 2009/0105785 A1 | 4/2009 | Wei et al. |
| 2009/0187159 A1 | 7/2009 | Greger et al. |
| 2010/0030129 A1 | 2/2010 | Nitzan et al. |
| 2010/0213070 A1 | 8/2010 | Oki et al. |
| 2010/0268287 A1 | 10/2010 | Celnik |
| 2010/0330589 A1 | 12/2010 | Bahrami et al. |
| 2011/0040291 A1 | 2/2011 | Weissenrieder-Norlin et al. |
| 2011/0054288 A1 | 3/2011 | Besio |
| 2011/0112590 A1 | 5/2011 | Molnar et al. |
| 2011/0118806 A1 | 5/2011 | Pascual-Leone et al. |
| 2011/0276112 A1 | 11/2011 | Simon et al. |
| 2011/0288610 A1 | 11/2011 | Brocke |
| 2011/0319975 A1 | 12/2011 | Ho et al. |
| 2012/0007832 A1 | 1/2012 | Lee et al. |
| 2012/0065699 A1 | 3/2012 | Bedenbaugh |
| 2012/0071947 A1 | 3/2012 | Gupta et al. |
| 2012/0078323 A1 | 3/2012 | Osorio |
| 2012/0184894 A1 | 7/2012 | Imran et al. |
| 2012/0191157 A1 | 7/2012 | Stypulkowski et al. |
| 2012/0226127 A1 | 9/2012 | Asjes et al. |
| 2012/0271377 A1 | 10/2012 | Hagedorn et al. |
| 2012/0289869 A1 | 11/2012 | Tyler |
| 2013/0085347 A1 | 4/2013 | Manicka et al. |
| 2013/0113059 A1 | 5/2013 | Song et al. |
| 2013/0184779 A1 | 7/2013 | Bikson et al. |
| 2013/0204315 A1 | 8/2013 | Wongsarnpigoon et al. |
| 2013/0261706 A1 | 10/2013 | Mirro et al. |
| 2013/0281759 A1 | 10/2013 | Hagedorn et al. |
| 2014/0069212 A1 | 3/2014 | Fishel et al. |
| 2014/0148872 A1 | 5/2014 | Goldwasser et al. |
| 2014/0172041 A1 | 6/2014 | Draghici et al. |
| 2014/0277324 A1 | 9/2014 | Diubaldi et al. |
| 2014/0296935 A1 | 10/2014 | Ferree et al. |
| 2014/0316505 A1 | 10/2014 | Yanaki |
| 2014/0350431 A1 | 11/2014 | Hagedorn |
| 2015/0005841 A1 | 1/2015 | Pal et al. |

(56) References Cited

U.S. PATENT DOCUMENTS

| | | |
|---|---|---|
| 2015/0065838 A1 | 3/2015 | Wingeier et al. |
| 2015/0066104 A1 | 3/2015 | Wingeier et al. |
| 2015/0088224 A1 | 3/2015 | Goldwasser et al. |
| 2015/0238759 A1 | 8/2015 | Katsnelson |
| 2015/0238762 A1 | 8/2015 | Pal et al. |
| 2015/0328467 A1 | 11/2015 | Demers et al. |
| 2015/0335877 A1 | 11/2015 | Jeffery et al. |
| 2015/0352357 A1 | 12/2015 | Wei et al. |
| 2015/0352364 A1 | 12/2015 | Meffin et al. |
| 2015/0360027 A1 | 12/2015 | Bachinski et al. |
| 2015/0374971 A1 | 12/2015 | Dar et al. |
| 2015/0375007 A1 | 12/2015 | Takeuchi et al. |
| 2016/0017558 A1 | 1/2016 | French |
| 2016/0022981 A1 | 1/2016 | Wingeier et al. |
| 2016/0175589 A1 | 6/2016 | Wingeier |
| 2016/0184585 A1 | 6/2016 | Kealey et al. |
| 2016/0256105 A1 | 9/2016 | Boyle et al. |
| 2016/0303362 A1 | 10/2016 | Wu et al. |
| 2016/0346530 A1 | 12/2016 | Jeffery et al. |
| 2016/0360990 A1 | 12/2016 | Altshuler et al. |
| 2016/0361541 A1 | 12/2016 | Wingeier et al. |
| 2016/0366507 A1 | 12/2016 | Hou et al. |
| 2017/0021158 A1 | 1/2017 | Wingeier et al. |
| 2017/0182285 A1 | 6/2017 | Tyler et al. |
| 2017/0224978 A1 | 8/2017 | Lee |
| 2017/0224990 A1 | 8/2017 | Goldwasser et al. |
| 2017/0224991 A1 | 8/2017 | Wingeier et al. |
| 2017/0361096 A1 | 12/2017 | Wingeier |
| 2017/0368344 A1 | 12/2017 | Ironi et al. |
| 2018/0021565 A1 | 1/2018 | Dar et al. |
| 2019/0111255 A1 | 4/2019 | Errico et al. |
| 2020/0139117 A1 | 5/2020 | Zaitsu |

FOREIGN PATENT DOCUMENTS

| | | |
|---|---|---|
| EP | 2449961 A1 | 5/2012 |
| GB | 2524816 A | 10/2015 |
| JP | 2010152731 A | 7/2010 |
| KR | 20150088224 A | 7/2015 |
| KR | 101685124 B1 | 12/2016 |
| KR | 20170021158 A | 2/2017 |
| KR | 20170028197 A | 3/2017 |
| KR | 20180021565 A | 3/2018 |
| WO | 2013113059 A | 3/1871 |
| WO | 2008048471 A2 | 4/2008 |
| WO | 2008075250 A1 | 6/2008 |
| WO | 2009134763 A1 | 11/2009 |
| WO | 2009138961 A1 | 11/2009 |
| WO | 2013004763 A1 | 1/2013 |
| WO | 2013113059 A1 | 8/2013 |

* cited by examiner

METHOD AND SYSTEM FOR IMPROVING PROVISION OF ELECTRICAL STIMULATION

CROSS-REFERENCE TO RELATED APPLICATIONS

This application is a continuation of U.S. patent application Ser. No. 15/426,212, filed 7, Feb. 2017, which claims the benefit of U.S. Provisional Application Ser. No. 62/292,511 filed 8, Feb. 2016 and U.S. Provisional Application Ser. No. 62/442,350 filed 4, Jan. 2017, which are each incorporated in their entireties herein by this reference.

TECHNICAL FIELD

This invention relates generally to the neuromodulation field, and more specifically to a new and useful method for improving provision of electrical stimulation.

BACKGROUND

Electrode systems in the neuromodulation field are used to transmit electrical signals to a subject, and can be used to detect or measure signals from the subject. Current electrode systems for electrical stimulation and/or signal detection are, however, insufficient for many reasons including inadequate monitoring of stimulation-associated parameters during stimulation, lack of safety features in a non-clinical setting, inadequate contact between the subject and the electrode(s) of a system, inadequate notification and/or guidance of the subject when contact is inadequate, non-robust contact between the subject and the electrode(s) of a system, subject discomfort while using an electrode system, and/or limited use within multiple electrical simulation or biosignal detection paradigms. Furthermore, methods of providing electrical stimulation also fail to provide a positive user experience, fail to properly mitigate effects of voltage or current transients, and fail to provide control of other waveform aspects. As such, current neuromodulation systems are inadequate for many reasons.

Thus, there is a need in the neuromodulation field for a new and useful method and system for improving provision of electrical stimulation. This invention provides such a new and useful method and system.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1:
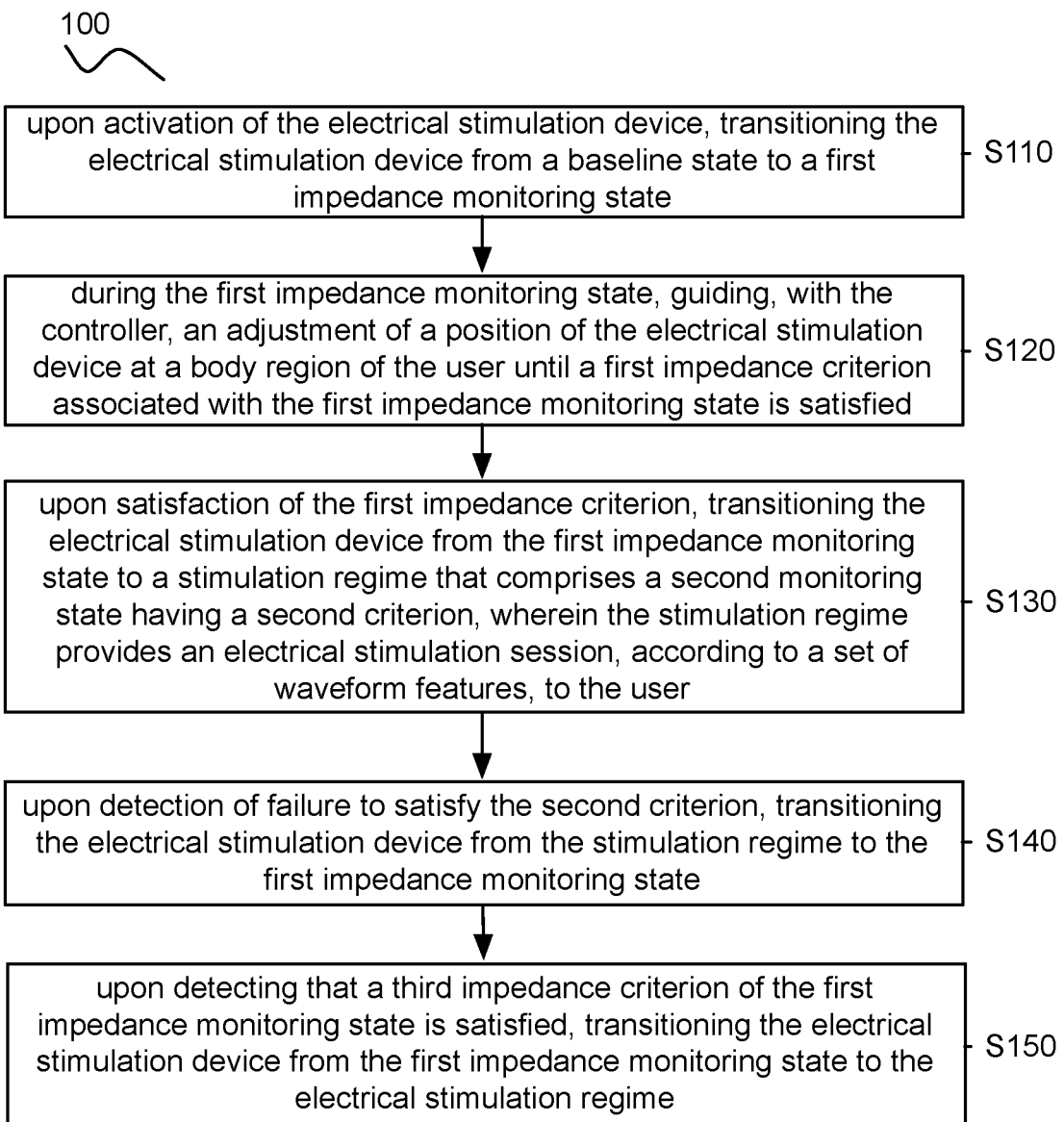
FIG. 1 depicts a schematic of an embodiment of a method for improving provision of electrical stimulation.

As shown in FIG. 1, an embodiment of a method 100 for providing electrical simulation to a user comprises: upon activation of the electrical stimulation device, transitioning the electrical stimulation device from a baseline state to a first impedance monitoring state S110; during the first impedance monitoring state, guiding, with the controller, an adjustment of a position of the electrical stimulation device at a body region of the user until a first impedance criterion associated with the first impedance monitoring state is satisfied S120; upon satisfaction of the first impedance criterion, transitioning the electrical stimulation device from the first impedance monitoring state to a stimulation regime that comprises a second monitoring state having a second criterion, wherein the stimulation regime provides an electrical stimulation session, according to a set of waveform features, to the user S130; upon detection of failure to satisfy the second criterion, transitioning the electrical stimulation device from the stimulation regime to the first impedance monitoring state S140; and upon detecting that a third impedance criterion of the first impedance monitoring state is satisfied, transitioning the electrical stimulation device from the first impedance monitoring state to the stimulation regime S150 (e.g., resuming the electrical stimulation session of Block S130).

The method 100 functions to provide means for impedance monitoring in electrical stimulation systems, with the goal of improving electrical stimulation treatment safety and/or efficacy. The method 100 can thus strategically and automatically monitor provision of an electrical stimulation treatment delivered to a user as the user performs training activities (e.g., athletic performance training, motor skills training, other training, other cognitive-associated tasks, etc.), wherein the electrical stimulation treatment is provided within specified treatment limits (e.g., for safety, in consideration of maximizing efficacy of the electrical stimulation treatment, etc.). However, the method 100 can additionally or alternatively function to increase an effect of an electrical stimulation treatment provided to the user or preemptively warn the user of conditions that might prevent the prescribed amount of neurostimulation from being delivered, by ensuring that the impedance parameters of the device-user body interface are within appropriate ranges during the course of a stimulation treatment.

In other variations, the method 100 can be used to enhance effectiveness of electrical stimulation in coordination with a user performing a task of interest, in order to enhance one or more of: motor ability (e.g., dexterity, coordination), memory (e.g., working memory, declarative memory), cognitive ability (e.g., mathematical ability), learning (e.g., language learning, speech learning), focus, attention, creativity, and/or any other suitable cognitive-associated attribute. In some specific applications, the method 100 can be used to increase neural plasticity in athletes who are attempting to improve performance in relation to a set of skills. Additionally or alternatively, the method 100 can be used to increase neural plasticity in stroke patients during rehabilitation, to improve the efficacy of therapy sessions for patients with paralyzing neurological disorders, and/or to increase neural plasticity in elderly users.

Preferably, at least a portion of the method 100 is configured to be implemented for a user who is outside of a clinical (e.g., hospital) or research (e.g., laboratory) setting, such that the user can be in a non-contrived environment as he or she is performing the set of tasks and/or receiving the electrical stimulation treatment. Additionally or alternatively, the method 100 can be implemented in an entirely clinical or research setting, such as a physical therapy clinic.

The method can be implemented, at least in part, using a system including an electrical stimulation device having a body-mountable portion and a set of electrodes coupled to the body-mountable portion, the electrical stimulation device operable between a baseline state, a first impedance monitoring state, and a stimulation regime having a second monitoring state, wherein the first impedance monitoring state includes a first set of impedance criteria and is enterable upon at least one of: a) detection of activation of the electrical stimulation device and b) failure to satisfy an impedance criterion of the second monitoring state, during the stimulation regime, and wherein the stimulation regime provides a stimulation session with a waveform definition to the head region of the user upon satisfaction of at least one of the first set of impedance criteria of the first impedance monitoring state. The system can further include a controller that transmits the stimulation waveform definition and guides adjustment of the set of electrodes at the head region of the user in cooperation with the first impedance monitoring state.

As such, the method 100 can be implemented by a system that is portable and comfortably worn by the patient as the patient performs the set of tasks (e.g., athletic performance training tasks, memory improving tasks, etc.). The method 100 can be implemented, at least in part, using embodiments, variations, and examples of the systems described in Section 2 below and/or in U.S. application Ser. No. 14/470,683 titled "Electrode System for Electrical Stimulation" and filed on 27, Aug. 2014, U.S. application Ser. No. 14/470,747 titled "Method and System for Providing Electrical Stimulation to a User"; U.S. App. No. 62/292,511 titled "Stimulation System and Method" and filed on 8, Feb. 2016; U.S. App. No. 62/442,350 titled "Stimulation System and Method" and filed on 4, Jan. 2017; U.S. application Ser. No. 14/878,647 titled "Electrode System for Electrical Stimulation" and filed on 8, Oct. 2015; U.S. application Ser. No. 15/059,095 titled "Method and System for Providing Electrical Stimulation to a User" and filed on 2, Mar. 2016; and U.S. application Ser. No. 15/335,240 titled "Electrode Positioning System and Method" and filed on 26, Oct. 2016, which are each incorporated herein in their entireties by this reference. The method 100 can, however, be implemented using any other suitable stimulation system with a controller (e.g., wearable stimulation system).

1.1 Method—Impedance Monitoring and Device Positioning

Block S110 recites: upon activation of the electrical stimulation device, transitioning the electrical stimulation device from a baseline state to a first impedance monitoring state. Block S110 functions to provide an initial regime of impedance checking when the electrical stimulation device is ready for use, in order to facilitate proper positioning of the device at the body region of the user in Block S120.

The electrical stimulation device of Block S110 preferably comprises an electrical stimulation device including a head-mountable portion coupled either reversibly or permanently to one or more electrodes, the electrical stimulation device in communication with a controller (e.g., a controller at least partially implemented using an application executing at a mobile computing device of the user). Embodiments, variations, and examples of a stimulation system are described in one or more of U.S. application Ser. No. 14/470,683 titled "Electrode System for Electrical Stimulation" and filed on 27, Aug. 2014, U.S. application Ser. No. 14/470,747 titled "Method and System for Providing Electrical Stimulation to a User"; U.S. App. No. 62/292,511 titled "Stimulation System and Method" and filed on 8, Feb. 2016; U.S. App. No. 62/442,350 titled "Stimulation System and Method" and filed on 4, Jan. 2017; U.S. application Ser. No. 14/878,647 titled "Electrode System for Electrical Stimulation" and filed on 8, Oct. 2015; U.S. applicaion Ser. No. 15/059,095 titled "Method and System for Providing Electrical Stimulation to a User" and filed on 2, Mar. 2016; and U.S. application Ser. No. 15/335,240 titled "Electrode Positioning System and Method" and filed on 26, Oct. 2016, which are each incorporated herein in their entireties by this reference; however, the electrical stimulation device can additionally or alternatively include any other suitable electrode positioning aspects and/or electrodes for providing stimulation. For instance, variations of the method 100 can be used for impedance monitoring in any other electrical stimulation device for any other suitable body region of a user, in relation to any other suitable type of treatment.

The baseline state of the electrical stimulation device is preferably a non-stimulating state, or a state in which current through the stimulation path is below a threshold level for stimulation. In examples, the baseline state can be a deactivated state, a powered-off state, an idling state, a standby state or any other suitable state. Transitioning from the baseline state to the first impedance monitoring state can be triggered with transmission of the waveform definition for stimulation from the controller to the electrical stimulation device; however, transitioning from the baseline state to the first impedance monitoring state (or any other state of the electrical stimulation device) can be triggered in any other suitable manner. In examples, transitioning from the baseline state can occur with any one or more of: receiving a user input (e.g., at the controller, at the device) to turn the electrical stimulation device from a powered-off state to an active state, receiving a user input (e.g., at the controller, at the device) to turn the electrical stimulation device from an idling state to an active state, receiving a user input (e.g., at the controller, at the device) to turn the electrical stimulation device from a standby state to an active state, detection of a change in the position of the electrical stimulation device (e.g., from a resting position to a position at the body of the user) with one or more motion sensors (e.g., accelerometers, gyroscopes, image-based sensors, audio-based sensors, temperature-based sensors, force sensors, pressure sensors, etc.), and any other suitable trigger.

The first impedance monitoring state preferably provides monitoring of impedance along a path of stimulation, according to a waveform definition prescribed for the electrical stimulation session of Block S130. As such, transitioning the electrical stimulation device from the baseline state to the first impedance monitoring state can include implementing a path impedance operation that provides monitoring of impedance according to one or more criteria, along the stimulation pathway (e.g., in relation to different electrodes, in relation to electrode regions, in relation to an interface between the electrode(s) and the body of the user, etc.). In addition to or in place of monitoring of impedance along a path of stimulation, the first impedance monitoring state may provide monitoring of impedance through one or more other paths, such as the set of paths in which each path is between two adjacent electrical segments of a single physical electrode, or the set of paths in which each path is between one electrode and the combined set of all other electrodes.

Figure 2:
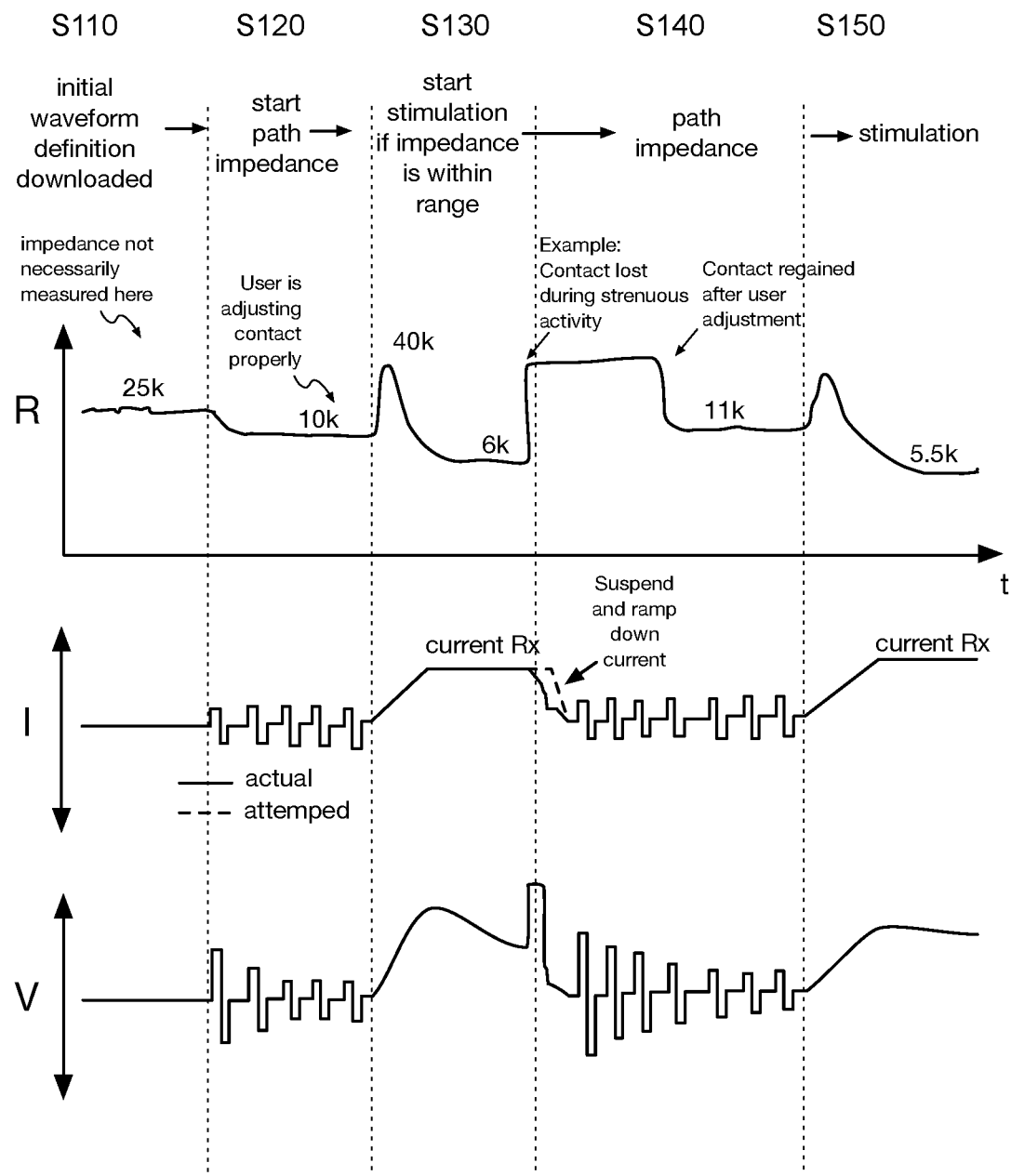
FIG. 2 depicts an example of impedance, current, and voltage behavior in an example of a method for improving provision of electrical stimulation.

As shown in FIG. 2, in an example application of Block S110, upon activation of the electrical stimulation device (e.g., turning the stimulation device on), a user can position a head-mountable portion of the electrical stimulation device (e.g., a headset) at his/her head region, with electrodes of the head-mountable portion positioned approximately near an intended position for stimulation. Prior to adjusting the position of the electrodes coupled to the head-mountable portion, impedance (R) through the stimulation path to the user may be high. In the example, activation of the electrical stimulation device includes transmission of a waveform definition from the controller to the electrical stimulation device, which governs the electrical stimulation session described in examples of Block S130. In the example, after transmission of the waveform definition, the controller commands the electrical stimulation device to initiate measurement of impedance along a path according to the waveform definition, according to a path impedance monitoring operation. However, alternative examples of Block S1$io$ can be implemented in any other suitable manner. For example, prior to adjusting the position of the electrodes coupled to the head-mountable portion, impedance (R) through the stimulation path to the user may be low, where this low impedance indicates that the position of the electrodes is not optimal (e.g. the electrodes are too close to each other or are shorted together). In another example, prior to adjusting the position of the electrodes coupled to the head-mountable portion, the complex impedance (Z, not shown) or frequency-dependent complex impedance (Z(f), not shown) through the stimulation path may not fall within a desirable range (e.g. a range that indicates that the electrodes are making contact with a correct anatomical region of the head, based on comparison with known electrical impedance tomology and/or electrical impedance plethysmographic data; a range that indicates that the size or electrical properties of the electrode-tissue interface are desirable for beginning stimulation). In general, the use of impedance herein may alternatively or additionally include complex impedance or frequency-dependent complex impedance in addition to conventional resistance. This complex impedance may be measured using techniques such as delivery of sinusoidal waveforms at varying or superimposed frequencies, or by extraction of complex impedance information from the shape of voltage transients produced by delivery of current pulses.

Block S120 recites: during the first impedance monitoring state, guiding, with the controller, an adjustment of a position of the electrical stimulation device at a body region of the user until a first impedance criterion associated with the first impedance monitoring state is satisfied. Block S120 functions to coordinate impedance monitoring with readjustment of the electrical stimulation device until impedance along the stimulation path is low enough to improve chances of having a non-disrupted stimulation session in Block S130.

In coordination with adjustment of the position of the electrical stimulation device at the body of the user, Block S120 can include outputting, through the electrical stimulation device, one or more current pulses, during which voltage parameters and/or current parameters can be monitored to determine impedance along the stimulation path(s). Block S120 preferably includes outputting a set of current pulses throughout the adjustment period, but can alternatively include outputting a single current pulse during the readjustment period. Alternatively, the outputted pulses can be voltage pulses, during which current parameters and/or voltage parameters can be monitored to determine impedance along the stimulation path(s).

In variations wherein a set of current pulses is output by the electrical stimulation device, the set of current pulses can include pulses having uniform pulse width, or can alternatively include pulses having non-uniform pulse widths (e.g., one or more pulses can have a width different than other pulses in the set of current pulses. Additionally or alternatively, each pulse in the set of pulses can have an identical amplitude to other pulses in the set of pulses (e.g., 0.18 mA zero-to-peak amplitude, zero-to-peak amplitude from 0.01 mA to 0.50 mA, etc.), or can alternatively, one or more pulses in the set of pulses can have a non-identical amplitude to other pulses in the set of pulses. The set of current pulses can additionally or alternatively be provided at a constant frequency (e.g., with constant time spacing between pulses, at a frequency between 2 and 20 Hz, etc.), or can alternatively be provided with non-uniform time spacing between pulses (e.g., random time spacing between pulses). Still alternatively, current pulses can be output whenever a sensor (e.g., accelerometer, gyroscope, magnetometer, force sensor, etc.) of the electrical stimulation device detects a change in position of the electrical stimulation device during the first impedance monitoring state. For instance, a current pulse or set of current pulses can be output after each of a set of adjustments to the position of the electrical stimulation device, detected by way of an above threshold motion of the electrical stimulation device detected using accelerometers. However, the set of current pulses can be output in any other suitable manner.

Figure 3:
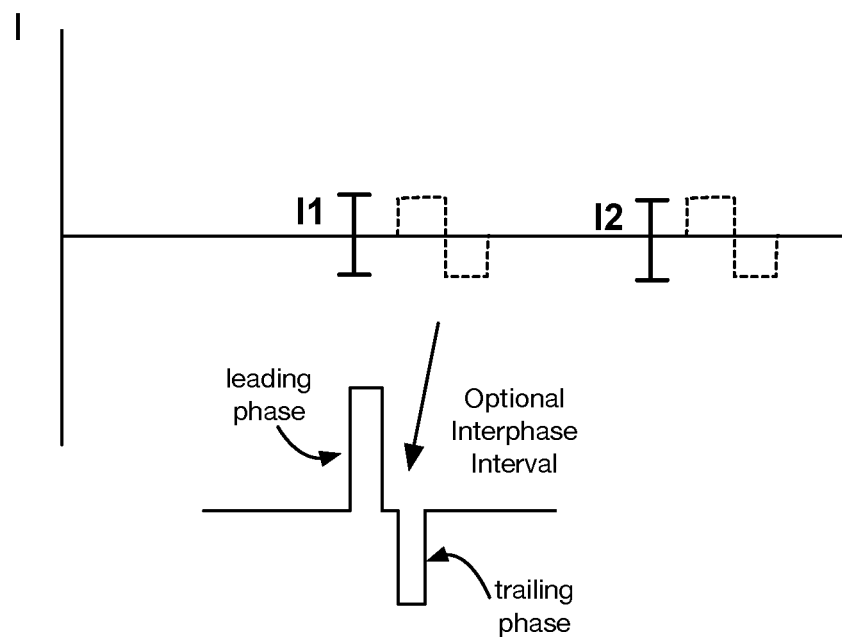
FIG. 3 depicts an example current pulse output in an embodiment of a method for improving provision of electrical stimulation.

The set of current pulses preferably comprise biphasic current pulses, an example of which is shown in FIG. 3, in order to avoid bias in impedance measurements produced using constant currents or monophasic pulses, and/or to facilitate controlled studies using sham electrical stimulation consisting at least in part of simulated stimulation whose actual amplitude is zero or very low, during which impedance and problems with electrode position must be detected in a realistic manner, embodiments, variations, and examples of which are described in U.S. application Ser. No. 14/470,683 titled "Electrode System for Electrical Stimulation". However, the set of current pulses can additionally or alternatively include one or more monophasic pulses, pseudomonophasic pulses, or pulses having alternative shapes.

In using biphasic current pulses, the set of pulses can include biphasic pulses including interphase intervals, or can include biphasic pulses without interphase intervals. During an interphase interval, the electrodes may optionally be shorted together internal to the device. Furthermore, the biphasic pulses can have a square-wave profile, an example of which is shown in FIG. 3. However, other variations, the biphasic pulses can have any other suitable profile (e.g., sawtooth profile, etc.).

Figure 4:
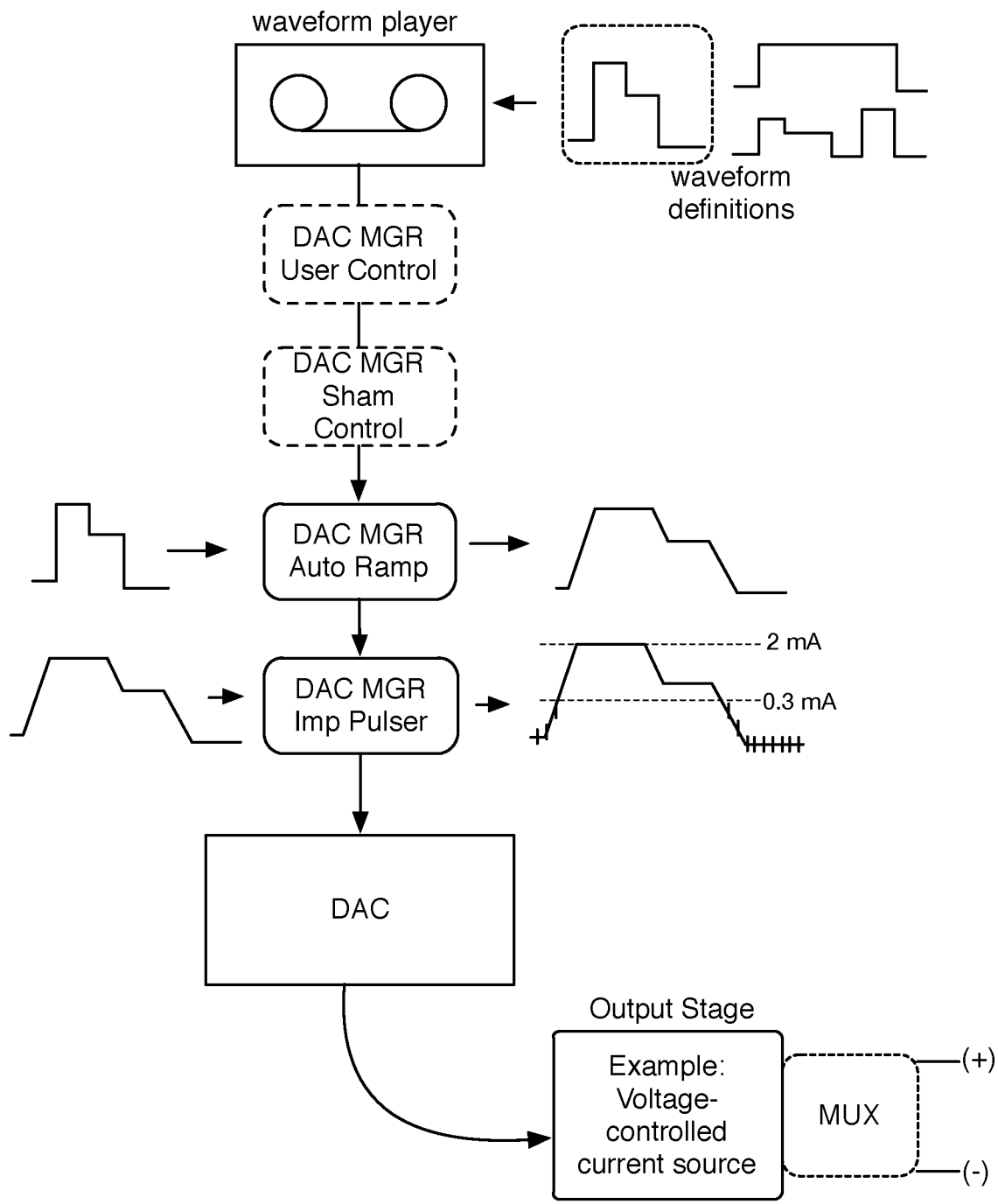
FIG. 4 depicts variations of components implemented in a method for improving provision of electrical stimulation.

In variations, implementing the first impedance monitoring state can include implementing elements (e.g., components in software, components in hardware, components in firmware) for management of one or more digital-to-analog converters (DACs) of the electrical stimulation device, wherein the DACs transform a digital waveform definition from the controller to an analog output (e.g., to an output stage that comprises a voltage-controlled current source including an amplifier operable to take an input voltage from the DAC and produce a controlled current through the stimulation path in proportion to the input voltage, to the electrodes of the electrical stimulation device used for stimulation). As such, as shown in FIG. 4, one or more of Blocks S110 and S120 can include implementing a first DAC management component that produces the set of current pulses for impedance monitoring as described above. In variations, the first DAC management component can be implemented in software and produce biphasic pulses whenever a portion of the waveform definition (or impedance monitoring state) has a value below a threshold current value, such that impedance through the stimulation path(s) can be checked (e.g., using total peak-to-peak voltage divided by total peak-to-peak current) even when current output is low. In a specific example, the current threshold is 0.3 mA, such that the first DAC management component with the DAC governs/controls output of biphasic current pulses whenever the current output is below 0.3 mA; however, in variations of the specific example, the current threshold for the first DAC management component can have any other suitable current value or range of values (e.g., from 0 mA to 1 mA, etc.). In variations, the DAC and output stage are both only capable of generating monophasic or substantially monophasic pulses, and/or output of a single polarity or of substantially a single polarity; in these variations, a biphasic output current pulse can be generated by use of multiplexing switches positioned functionally between the output stage and the user, such that the polarity is switched between the leading phase and the trailing phase.

As such, in examples of Block S110, biphasic current pulses are output during the first impedance monitoring state whenever the amount of current that is delivered through the stimulation pathway (e.g. as specified by a waveform definition), is below a threshold amount of current; however, the set of current pulses can additionally or alternatively be delivered in any other suitable manner.

The first impedance criterion of the first impedance monitoring state is preferably an impedance or resistance-based criterion that involves measurement of impedance in non-stimulating regimes of the electrical stimulation device. In one variation, impedance can be determined as a total peak-to-peak voltage measured during a biphasic pulse divided by a total peak-to-peak current output during the biphasic pulse. In another variation, impedance/resistance can be measured in any other suitable manner.

In still other variations, impedance can alternatively be indirectly inferred based upon the amount of current that can actually be delivered through the stimulation path(s). However, impedance monitoring can be implemented in another manner in Block S120.

The first impedance criterion is preferably more stringent than the third impedance criterion used in Block S150, as described in more detail below, in order to provide more stringent requirements for initializing stimulation, in comparison to re-initializing stimulation if, for some reason, impedance increases above a threshold limit during the stimulation regime. In practice, greater stringency in the first impedance criterion, as compared to the third impedance criterion, can be based upon difficulty of achieving the impedance criterions. For instance, because impedance may drop after the initial onset of stimulation, setting the same impedance threshold for both the first impedance criterion and the third impedance criterion produces an easier to achieve third impedance criterion (i.e., after the stimulation session has begun or progressed). However, the first impedance criterion can alternatively be identical to the third impedance criterion of Block S150, or can alternatively be less stringent than the third impedance criterion of Block S150. For instance, the device can be configured such that prior to entering the stimulation regime of Block S130, the measured impedance must be below a threshold limit of 10 kΩ (e.g., a first impedance criterion), but after stimulation has been interrupted in Block S140, re-initializing stimulation can occur when the measured impedance is below a threshold limit of 12 kΩ (e.g., a third impedance criterion). However, the first impedance criterion and the third impedance criterion can additionally or alternatively have any other suitable impedance threshold values (e.g., 1 kΩ, 5 kΩ, 10 kΩ, 15 kΩ, etc.) or any other suitable range of threshold conditions for impedance (e.g., 5-10 kΩ, 8-12 kΩ, etc.)

Figure 5:
FIG. 5 depicts an example of an application feature implemented in a method for improving provision of electrical stimulation.

In relation to guiding the adjustment of the position of the electrical stimulation device at the body of the user in Block S120, Block S120 can include guiding the user to manually position the electrical stimulation device using one or more of: visual guidance, auditory guidance, haptic guidance, and any other suitable form of guidance. In a first variation, a display of the controller (e.g., a display of a mobile computing device along with an application executing at the mobile computing device) can be configured to provide live guidance for dynamically adjusting the position of the electrical stimulation device, examples of which are shown in FIG. 5. Additionally or alternatively, in another variation, wherein the electrical stimulation device comprises a headset that positions electrodes at the head of the user, audio output devices (e.g., beeping elements, speaker elements, etc.) coupled to the headset can be configured to provide guidance in relation to positioning of the headset. In a first example, one or more of beeping frequency, pitch, and loudness, or vibration frequency or amplitude, can be reduced as the headset approaches an optimized position. In another example, verbal instructions can be delivered through speakers of the headset. However, guidance for manual adjustment can be provided in Block S120 in any other suitable manner.

Alternatively, Block S120 can additionally or alternatively include automatic adjustment of the electrical stimulation device to provide suitable impedance through the stimulation path(s) to initialize stimulation in Block S130. In one such example, Block S120 can include implementing vibration motors (e.g., eccentric rotating mass devices) operable to vibrate the electrical stimulation device (e.g., a headset portion of the electrical stimulation device) at the body of the user until the first impedance criterion is achieved. However, automatic adjustment of the position of the electrical stimulation device can be achieved in Block S120 in any other suitable manner.

As shown in FIG. 2, in an example application of Block S120, once a path impedance operation has been initiated (in the example of Block S110 above), the electrical stimulation device can be configured to produce biphasic current pulses, in coordination with measurement of impedance by the electrical stimulation device, wherein the impedance is measured by dividing the total peak-to-peak voltage measured during a biphasic pulse by the total peak-to-peak current output during the biphasic pulse. The example application thus allows for collection of a high-quality impedance measurement, even if interfaces involving the electrode (e.g., an electrode-to-tissue interface, an electrode-to-saline interface, etc.) develop electrochemical potentials that could otherwise affect impedance determination. The example of Block S120 described thus implements an impedance/resistance-focused criterion, rather than a current-focused criterion associated with how much current can actually be delivered through the stimulation pathway.

In the example application of Block S120 above, and concurrent with the biphasic pulse-based impedance measurements, the example can further include guiding the user, within an application executing at the mobile computing device of the user (i.e., the controller), to adjust the position of a head-mountable portion of the electrical stimulation device until contact between electrodes coupled to the head-mountable portion and the user's head is improved. Guiding, in the example, can include rendering a representation of the head-mountable portion of the electrical stimulation device along with representations of electrodes relative to the head-mountable portion, with indications of which electrodes have poor contact, an example of which is shown in FIG. 5. Upon achieving an impedance value lower than a threshold impedance value (e.g., 16 k$\Omega$, 5-25 k$\Omega$, etc.) the example application of the method 100 can include transitioning the electrical stimulation device from the first impedance monitoring state to the stimulation regime, as described in relation to Block S130 below. However, alternative examples of Block S120 can implement any other suitable impedance criterion for initializing stimulation according to Block S130, or otherwise be implemented in any other suitable manner. In an example, the impedance criterion of Block S120 and/or other impedance criteria described herein may also be implemented as two-part criteria involving hysteresis, in order to reduce rapid cycling between an impedance monitoring state and an electrical stimulation regime. For example, the impedance criterion could require that impedance initially fall below an initial threshold, such as 15 k$\Omega$, however briefly, but remain under a somewhat higher threshold, such as 20 k$\Omega$, for a duration such as five seconds in order to exit the impedance monitoring state.

1.2 Method—Stimulation and Impedance Monitoring

Block S130 recites: upon satisfaction of the first impedance criterion, transitioning the electrical stimulation device from the first impedance monitoring state to a stimulation regime that comprises a second monitoring state having a second criterion, wherein the stimulation regime provides an electrical stimulation session, according to a set of waveform features, to the user. Block S130 functions to initiate and provide a session of stimulation, once impedance along the stimulation path(s) is suitable according to Blocks S110 and S120.

Transitioning the electrical stimulation device to the stimulation regime preferably includes implementing a stimulation session according to the waveform definition transmitted to the electrical stimulation device by the controller.

In variations, implementing the stimulation session according to the waveform definition can include implementing elements (e.g., components in software, components in hardware, components in firmware) for management of one or more digital-to-analog converters (DACs) of the electrical stimulation device, wherein the DACs transform a digital waveform definition from the controller to an analog output (e.g., to an output stage that comprises a voltage-controlled current source including an amplifier operable to take an input voltage from the DAC and produce a controlled current through the stimulation path in proportion to the input voltage, to the electrodes of the electrical stimulation device used for stimulation).

As such, as shown in FIG. 4, Block S130 can include implementing a second DAC management component that modulates waveform components involving abrupt transitions in current output (e.g., abrupt transitions from a high current state to a low current state or from a low current state to a high current state), in order to improve user comfort associated with the electrical stimulation provided. The second DAC management component thus ramps down current and/or ramps up current according to a desired ramp rate, for features of the waveform definition that have an above threshold change (e.g., a maximum step value) in current value. In an example, the second DAC management component is implemented as a software object that tracks step changes in current delivered and, if a step change in current is detected, the second DAC management component transforms the step change into an appropriate ramped up or ramped down change in current, in order to enhance user comfort.

The threshold change in current that triggers current ramping by the second DAC management component can be a fixed threshold across multiple users, or can alternatively be user-specific or demographic specific. For instance, in an example, the threshold change in current before ramping occurs can be set by a user during calibration of the electrical stimulation device, wherein the user can experience different step changes in current and indicate the step size at which discomfort begins. In another example, biological parameters of the user (e.g., skin thickness, touch receptor distribution, etc.) can be used to determine an appropriate threshold value. In another example, the threshold change in current before ramping occurs could be set by the waveform definition, and/or modified during the course of waveform delivery by data in the waveform definition. However, the threshold change can alternatively be determined in any other suitable manner.

In variations of the second DAC management component, the ramp rate can be constant regardless of the current step size. Alternatively, the ramp rate parameters can depend upon the current step size (e.g., an inverse relationship can exist between step size and ramp rate). Furthermore, the ramp rate for ramping up current can be the same as or different from the ramp rate for ramping down current. Additionally or alternatively, the ramp can include a linear ramp or a non-linear ramp. However, transforming a waveform definition by the second DAC management component can alternatively be implemented in any other suitable manner.

Additionally or alternatively, the second DAC management component can modulate waveform components including abrupt transitions from a state where the current waveform is of low energy (e.g., zero output, or an oscillatory waveform of RMS value 0.1 mA) to a state where the current waveform is of high energy (e.g., an oscillatory waveform of RMS value 1.0 mA), or vice-versa from high energy to low energy. This embodiment of the second DAC management component thus ramps down overall scaling, energy, or RMS value of the delivered waveform and/or ramps up overall scaling, energy, or RMS value of the delivered waveform according to a desired ramp rate.

Additionally or alternatively, a third DAC management component, as shown in FIG. 4, can be included in the system of Block S130, in order to deliver sham stimulation in the course of e.g. a clinical trial. This third DAC management component can act to divert stimulation current through an internal shorted path, or to replace the stimulation output prescribed by the waveform definition with a zero-amplitude or low-amplitude sham output while simultaneously collecting impedance data and producing realistic system behavior such as alerting the user if connection to the head is lost. This third DAC management component can be enabled by the user, or remotely, or may be enabled and disabled by data contained within the waveform definition. Additionally or alternatively, a fourth DAC management component, as shown in FIG. 4, can be included in the system of Block S130, in order to scale stimulation output according to user input. This scaling may be accomplished e.g. by applying a predefined multiplier or a multiplier specified by the waveform definition to the DAC output for each of a set of amplitude levels selectable by the user (e.g., using a knob or slider control element on a user interface on a controller 220), embodiments, variations, and examples of which are described in U.S. application Ser. No. 15/059,095 filed 2, Mar. 2016, which is herein incorporated in its entirety by this reference.

The stimulation session of the stimulation regime is preferably implemented using electrodes wetted with saline; however, the stimulation session of the stimulation regime can alternatively be implemented using any other suitable type(s) of electrodes. In embodiments, variations, and examples, stimulation is carried out using electrodes as described in one or more of: U.S. application Ser. No. 14/470,683 titled "Electrode System for Electrical Stimulation" and filed on 27, Aug. 2014; U.S. application Ser. No. 14/470,747 titled "Method and System for Providing Electrical Stimulation to a User"; U.S. App. No. 62/292,511 titled "Stimulation System and Method" and filed on 8, Feb. 2016; U.S. App. No. 62/442,350 titled "Stimulation System and Method" and filed on 4, Jan. 2017; U.S. application Ser. No. 14/878,647 titled "Electrode System for Electrical Stimulation" and filed on 8, Oct. 2015; U.S. application Ser. No. 15/059,095 titled "Method and System for Providing Electrical Stimulation to a User" and filed on 2, Mar. 2016; and U.S. application Ser. No. 15/335,240 titled "Electrode Positioning System and Method" and filed on 26, Oct. 2016; however, Block S130 can additionally or alternatively implement any other suitable electrode system, or any system of transducers such as ultrasound or light-emitting elements for brain stimulation.

The stimulation session of the stimulation regime of Block S130 preferably includes transcranial electrical stimulation (TES) configured to stimulate a brain region of the user in the form of at least one of: transcranial direct current stimulation (tDCS), transcranial alternating current stimulation (tACS), transcranial magnetic stimulation (TMS), transcranial random noise stimulation (tRNS), transcranial variable frequency stimulation (tVFS), and any other suitable form of transcranial stimulation.

In variations the waveform of the stimulation regime of Block S130 can be associated with one or more of: direct current (DC) stimulation; alternating current (AC) stimulation; pulse trains, random stimulation; pseudorandom stimulation; substantially pseudorandom noise stimulation; band-limited random noise stimulation; band-limited pseudorandom noise stimulation; variable frequency stimulation (VFS); stimulation with composite superposed waveforms; and any other suitable type of stimulation. The waveform(s) of the stimulation can be defined by parameters including one or more of: amplitude, frequency, spectrum, pulse width, inter-pulse interval, and any other suitable parameters, wherein the parameter(s) are constant over at least a portion of the waveform. Additionally or alternatively, in some variations of Block S130, the parameter(s) of the waveform can vary over at least a portion of the waveform. However, Block S130 can include providing stimulation treatment with any other suitable type of waveform, embodiments, variations, and examples of which are described in U.S. application Ser. No. 14/470,747 titled "Method and System for Providing Electrical Stimulation to a User".

The stimulation session of the stimulation regime of Block S130 can additionally or alternatively implement method steps for waveform transformation, embodiments, variations, and examples of which are described in U.S. application Ser. No. 15/059,095 titled "Method and System for Providing Electrical Stimulation to a User" and filed on 2, Mar. 2016. However, the stimulation session of the stimulation regime of Block S130 can additionally or alternatively be implemented in any other suitable manner.

In relation to the second monitoring state of Block S130, the second criterion can include a current-focused criterion. In one variation, the current-focused criterion can measure impedance by dividing actual stimulation voltage (V) by actual stimulation current ($i_{actual}$). In another variation, the current-focused criterion can include monitoring of a difference between the current that is attempted to be delivered ($i_{attempted}$), and the actual current ($i_{actual}$) that is delivered. In specific examples, the difference threshold can be an absolute difference or can alternatively be a percent difference (e.g., 10% difference between $i_{actual}$ and $i_{attempted}$), or can be defined as the larger of a percent difference and an absolute difference (e.g., 10% or 0.1 mA difference, whichever is greater). As such, the second criterion can be associated with a determination of how much current can actually be delivered in a specific configuration of the electrical stimulation device at the body of the user. In this variation, if the actual current ($i_{actual}$) less than the current that is attempted to be delivered is ($i_{attempted}$) by an above-threshold amount, the second criterion is not satisfied and Block S140 is implemented. However, as long as the current that is attempted to be delivered ($i_{attempted}$) is within a threshold range of the actual current ($i_{actual}$) that is delivered, the second criterion is satisfied and the stimulation session of the stimulation regime of Block S130 continues. The second impedance can additionally or alternatively have a duration factor (e.g., an impedance or current threshold condition must be sustained for a certain period of time before stimulation is paused, or must be observed for a certain number of measurements in a certain time window); however, the second monitoring criterion (and/or the first impedance monitoring criterion) can additionally or alternatively have any other suitable conditions.

Additionally or alternatively, the stimulation regime of Block S130 can implement the first DAC management component to produce biphasic current pulses (or other current pulses) for impedance measurements (e.g., in low current portions of the waveform definition, etc.).

Additionally or alternatively, in relation to safety, the method and/or system described can implement a multiplexer (MUX) array with a set of internal switches (e.g., an analog switch solid state relay) configured to pass desired current outputs to electrodes for stimulation, and to short/route undesired current back to the system. As such, transients, anomalies, and/or undesired high currents can be safely routed through alternative pathways and away from the electrodes for stimulation, to protect the user from unsafe currents; for instance, if the system detects that the delivered current is higher than the current specified by the waveform definition by a given threshold, the system can react by shorting all outputs together, ensuring that no current reaches the user, while additionally alerting the user.

As shown in FIG. 2, in an example application of Block S130, once the controller of the system determines that the first impedance criterion has been satisfied (e.g., by comparing impedance to a threshold, by requiring that the threshold condition has not been satisfied for a certain duration of time), the controller can issue a command to transition from the first impedance monitoring state and to initialize the stimulation regime. In the specific example, the stimulation session includes a waveform definition component of direct current (DC) stimulation at a specific level, and because the DC level is above a threshold amount, the second DAC management component of the specific example implements a linear ramp to the DC level for user comfort. In the specific example, as the current is ramped to the DC level, the first DAC management component of the specific example produces biphasic pulses when the delivered current is below a current threshold (e.g., 0.3 mA) in order to provide accurate impedance measurements, but above the threshold current, impedance is measured by dividing actual stimulation voltage by actual stimulation current delivered. Once stimulation has started in the stimulation regime, measured impedance typically (but not necessarily) rises to a higher value over a short period of time due to electrochemical reactions at the electrode-to-tissue interface, and then typically (but not necessarily) drops gradually over the course of stimulation over a longer period of time (e.g., due to electrochemical reactions and biological effects, such as poration or vasodilation of tissue proximal to the electrodes), as shown in FIG. 3. However, variations of the specific example of Block S130 can operate in any other suitable manner or produce any other suitable behavior.

1.3 Method—Impedance Change Detection and Device Re-Adjustment

Block S140 recites: upon detection of failure to satisfy the second criterion, transitioning the electrical stimulation device from the stimulation regime to the first impedance monitoring state. Block S140 functions to stop stimulation or otherwise stop attempts to output a current for stimulation if current (e.g., in relation to measuring attempted vs. actual current) or impedance do not satisfy desired threshold criteria.

In Block S140, determining that the second criterion has not been satisfied can include: comparing actual current, $i_{actual}$, being delivered to attempted current, $i_{attempted}$, delivered and transitioning to the first impedance monitoring state if the difference between $i_{actual}$ and $i_{attempted}$ is above a threshold (e.g., a threshold percent difference, a threshold absolute difference, etc.). Additionally or alternatively, determining that the second criterion has not been satisfied can include determining impedance by dividing actual voltage by actual current, and transitioning to the first impedance monitoring state if the impedance is greater than a threshold impedance value. However, determining that the second criterion has not been satisfied can be performed in any other suitable manner.

In variations, failure to satisfy the second criterion can occur due to situations including one or more of: motion of the user during strenuous activity (e.g., performance of an athletic training regimen while coupled to the electrical stimulation device); motion of the user during non-strenuous activities (e.g., the electrical stimulation device slips from a position as the user moves about during a non-strenuous activity); removal of the electrical stimulation device (e.g., by the user, by another entity) due to discomfort during stimulation; removal of the electrical stimulation device (e.g., by the user, by another entity) due to intentions to prematurely stop stimulation; impedance-related failures due to electrode fouling; impedance-related failures due to electrode saturation state (e.g., by saline, etc, including increase of impedance due to drying.); impedance-related failures due to improper coupling between the electrodes and other portions of the electrical stimulation device; impedance-related failures due to system electrical system failure; and any other suitable situation that results in unsuitable impedance characteristics along the stimulation path(s).

Transitioning the electrical stimulation device from the stimulation regime to the first impedance monitoring state in Block S140 preferably includes implementing the second DAC management component described in Block S130 above, whereby the second DAC management component appropriately ramps the stimulation current down to below a threshold current level associated with the first impedance monitoring state. In this variation, ramping down the current promotes user comfort, such that jarring changes in current experienced at the electrode-tissue interface are not provided to the user. However, Block S140 can alternatively omit ramping down the current by way of a second DAC management component.

Additionally or alternatively, in relation to transitioning to the first impedance monitoring state, Block S140 can include implementing the first DAC management component to produce a set of current pulses for determining impedance in a low current state (or zero current state) of the electrical stimulation device. Similar to Block S110 above, the first DAC management component, with the DAC, can be configured to provide biphasic pulses with an optional interphase interval at a set frequency when the current drops below a threshold current limit, during the transition from the stimulation regime to the first impedance monitoring state. However, Block S140 can alternatively omit implementation of the first DAC management component and can operate in any other suitable manner.

Similar to Block S110 above, once the first impedance monitoring state has been arrived at (or prior to arrival at the first impedance monitoring state), the controller and/or the electrical stimulation device can be configured to guide adjustment of the electrical stimulation device at the body region of the user until proper impedance characteristics along the stimulation path(s) are achieved, similar to methods described in Blocks S110 and S120. However, guidance for adjusting the electrical stimulation device at the body region of the user can alternatively be implemented in any other suitable manner.

As shown in FIG. 2, in an example application of Block S140, once a head-mountable portion of the electrical stimulation device begins to lose contact with the head of the user (e.g., due to strenuous activity), impedance begins to rise to a level at which the voltage available to the output stage (to the electrodes) is insufficient to drive the attempted current, $i_{attemped}$, through the stimulation path(s), and the actual current, $i_{actual}$, delivered deviates from the attempted current, $i_{attempted}$. This condition is detected by the electrical stimulation device, which implements the second criterion by periodically monitoring (e.g., 10 times per second, once per second, etc.) and comparing $i_{attemped}$ to $i_{actual}$ and providing a current error output if $i_{attemped}$ and $i_{actual}$ differ by a threshold amount (e.g., 10%, 0.1 mA, any percent difference from 1-20%, any current difference from 0.02-0.5 mA, etc.), with a threshold frequency (e.g., $i_{attemped}$ and $i_{actual}$ are significantly different for 30% of measurements within a given 1-second window), or with a threshold number of sequential instances (e.g., 3 sequential differences between $i_{attemped}$ and $i_{actual}$).

As such, in the example of Block S140, when the current deviation is detected, the electrical stimulation device begins to ramp down the stimulation current according to a programmed maximum ramp slope (e.g., 0.3 mA per second) to transition from the stimulation regime to the first impedance monitoring state. Similar to the example described in relation to Blocks S110 and S120, the electrical stimulation device then begins providing biphasic current pulses, and the user is prompted to adjust position of the head mountable portion of the electrical stimulation device in manners similar to that described in Blocks S110 and S120 above.

In the example of Block S140 above, one or more of the electrical stimulation device and the controller can be configured to output one or more error notifications (e.g., visually with displays or light, haptically, audibly, etc.). For instance, one or more of the electrical stimulation device and the controller can provide a status condition or an error notification upon transition from the stimulation regime to the first impedance monitoring state. Additionally or alternatively, one or more of the electrical stimulation device and the controller can provide a status condition or an error notification if a parameter of the current delivered was too high (e.g., with no option to continue or restart stimulation). Additionally or alternatively, one or more of the electrical stimulation device and the controller can provide a status condition or an error notification if a parameter of the current delivered was too low (e.g., if the head-mountable portion of the electrical stimulation device loses contact with the head of the user). However, any other suitable status condition or error notification can be provided.

1.4 Method—Transitioning to Stimulation

Block S150 recites: upon detecting that a third impedance criterion of the first impedance monitoring state is satisfied, transitioning the electrical stimulation device from the first impedance monitoring state to the electrical stimulation regime. Block S150 functions to transition the electrical stimulation device back to the stimulation regime (or another appropriate state of the electrical stimulation device), once the impedance characteristics for the stimulation path(s) are below a given threshold for stimulation to begin.

In some variations, implementation of the first impedance monitoring state in Block S150 is similar to implementation of the first impedance monitoring state in Block S120. However, as indicated in Block S120 above, the third impedance criterion is preferably different from the first impedance criterion of Block S120. In one variation, the third impedance criterion is less stringent than the first impedance criterion, in order to provide more stringent requirements for initializing stimulation, in comparison to re-initializing stimulation after impedance increases above a threshold limit during the stimulation regime (e.g., due to lost contact during strenuous activity). Again, in practice, greater stringency in the first impedance criterion, as compared to the third impedance criterion, can be based upon difficulty of achieving the impedance criterions. For instance, because impedance may drop after the initial onset of stimulation, setting the same impedance threshold for both the first impedance criterion and the third impedance criterion produces an easier to achieve third impedance criterion (i.e., after the stimulation session has begun or progressed). In an example, the third impedance criterion and the first impedance criterion can each have an associated impedance threshold of 10 k$\Omega$, given that it is easier to achieve 10 k$\Omega$ in impedance once stimulation has begun or progressed. In another example, the third impedance criterion can have an associated impedance threshold of 12 k$\Omega$ to reinitialize stimulation, in comparison to a first impedance threshold of 10 k$\Omega$ required to start a new stimulation session. However, as indicated above, each of the first impedance criterion and the third impedance criterion can include a range of impedance values for starting stimulation (e.g., the first impedance criterion can have an associated range of 5-10 k$\Omega$ and the third impedance criterion can have an associated range of 8-13 k$\Omega$). Similar to the criteria described in Block S120 above, the impedance criterion of Block S150 can have a factor associated with duration or number of pulses. For instance, in a first example, the third impedance criterion can require that impedance remains below a threshold value for 5 seconds before stimulation re-initializes. In a second example, the third impedance criterion can require that impedance remains below a threshold value for 10 biphasic pulses. However, the third impedance criterion can additionally or alternatively have any other suitable conditions to provide proper performance of the electrical stimulation device and/or to enhance user safety.

Furthermore, the third impedance criterion can alternatively be identical to the first impedance criterion of Block S120, or can alternatively be more stringent than the first impedance criterion of Block S120.

Any one or more of the above Blocks, in relation to implementing the first impedance monitoring state, providing stimulation, monitoring impedance/current, leaving the stimulation regime, re-implementing the first impedance monitoring state, and/or re-entering the stimulation regime, can be implemented with involvement of the controller, or independently of the controller (e.g., at a head mountable portion of the electrical stimulation device). For instance, the method 100 can be implemented for a user who has placed the controller (e.g., a mobile device executing an application and, in some circumstances, in communication with the head mountable portion of the electrical stimulation device) at a remote location while performing a training activity with the head mountable portion of the electrical stimulation device. However, the method 100 can additionally or alternatively be implemented in any other suitable manner.

In relation to transitioning the electrical stimulation device to the electrical stimulation regime, Block S150 can include simply resuming the stimulation session at the point at which the stimulation session stopped in Block S140. Alternatively, Block S150 can include continuing stimulation according to a modified stimulation session, based on one or more factors including: duration of time for which stimulation was not provided to the user during Block S140; cause of high impedance; attempted current output before transitioning to the first monitoring state from the stimulation regime; user intentions (e.g., the user may not want to continue stimulation); amount of stimulation that the user has received in a given time period; detection of biometric parameters of the user (e.g., in relation to cardiovascular parameters, in relation to neurological parameters, in relation to respiratory parameters, in relation to parameters indicative of stress, etc.); and any other suitable factors.

For instance, in a first example, if the user's stimulation session has only been interrupted for below a threshold duration of time (e.g., 30 seconds), the stimulation session can resume at the point at which the stimulation session stopped in Block S140. Additionally or alternatively, if the user's stimulation session has been interrupted for above a threshold duration of time (e.g., 10 minutes), the stimulation session can be resumed with modifications (e.g., stimulation can be resumed at a time point before the point at which stimulation was interrupted, stimulation can be resumed with changes in intensity/amplitude, etc.). Additionally or alternatively, if the user's stimulation session was interrupted near the end of the stimulation session, the stimulation session may not be resumed because the desired effectiveness has been nearly achieved.

For instance, in some applications, it may be desirable that an aggregated amount of at least one stimulation parameter of the stimulation session provided during a time window does not exceed a maximum limit, for example, for safety reasons. As such, a maximum limit for an aggregated value of a stimulation parameter as related to Blocks S130-S150 can be any one or more of: a maximum dosage (e.g., duration of stimulation, aggregated charge, aggregated charge density, etc.) per day, a maximum dosage per shorter unit of time (e.g., minutes, hours), and any other suitable maximum dosage. In one example, a daily dosage of 30 minutes is an acceptable dosage of tDCS, with higher doses increasing chances of skin irritation for the user and/or other side effects. Furthermore, a remaining allowable stimulation can be tracked in relation to the maximum limit as an accumulated amount of stimulation subtracted from a maximum dosage of stimulation. Here, the accumulated dosage can be increased by additional electrical stimulation, and decreased (e.g., according to a logarithmic decay) when stimulation is not occurring. Thus, maximizing an effect of electrical stimulation treatment given a maximum acceptable limit of treatment can significantly benefit a user's recovery/rehabilitation/learning/improvement rate. In variations wherein the electrical stimulation treatment includes TES, the maximum limit is preferably a maximum amount of charge or charge density (e.g., determined based upon current amplitude, duration, duty cycle, and electrode path) that can be delivered to the user per unit time (e.g., the time window), or a maximum amount of total charge (e.g., current multiplied by total delivery time). Additionally or alternatively, the electrical stimulation provided within the time window can be transmitted and modulated such that at least a minimum amount of stimulation (i.e., defined as an amount below which stimulation has no effect) is always provided to the user within the time window. For example, a minimum duration and/or duty cycle of tDCS can always be provided to the user within the time window so that the electrical stimulation treatment provided to the user always has a measureable effect on the user's neural plasticity. As such, Blocks S130-S150 can enable transmission of a limited amount of electrical stimulation treatment to the user in a manner that automatically provides the user with electrical stimulation when the user needs electrical stimulation the most, and in a manner that has a measureable effect on the user's neurological condition. Again, in some variations, Blocks S130-S150 can substantially omit modulating the stimulation session according to a maximum limit constraint, in relation to interruptions to the session due to impedance-related factors.

Similar to methods described above, transitioning back to the stimulation session can include implementation of a second DAC management component that appropriately ramps up the current for the stimulation to a desired level. However, stimulation can alternatively be resumed in Block S150 without ramping or otherwise implementing a second DAC management component.

In an example application, as shown in FIG. 2, once the impedance falls below a threshold impedance value during the first impedance monitoring state (after, the electrical stimulation device can enter an idling state (e.g., a "Good to go" state); however, if impedance rises, the electrical stimulation device can enter a waiting state (e.g., a "suspend stimulation" state). Once a below threshold impedance value (e.g., 12 k$\Omega$) along the stimulation path is sustained for a certain duration of time, the electrical stimulation device can be transitioned back to the stimulation regime, resuming the stimulation session according to the waveform definition at the point of interruption.

In the example, the electrical stimulation device implements a second DAC management component to ramp up the current for stimulation according to a programmed maximum ramp slope (e.g., 0.3 mA per second) rather than immediately setting the attempted current value to the value of the current when stimulation was interrupted, according to the waveform definition. As shown in FIG. 2, as stimulation proceeds, impedance typically (but not necessarily) drops gradually over the course of stimulation due to electrochemical reactions and biological effects. Stimulation can then terminate normally according to the waveform definition, if no other current deviations or impedance deviations are experienced. Alternatively, the method 100 can repeat implementation of Blocks S130-S150 if another deviation in current or impedance is experienced.

In variations, the method 100 can omit or rearrange blocks described above, based upon situation or status of the electrical stimulation device. For instance, the method 100 can omit implementing the first impedance monitoring stage after stimulation has been interrupted due to high impedance, and instead implement other methods of detecting changes in position of the electrical stimulation device relative to the body of the user, and repositioning the electrical stimulation device. In one such example, the electrical stimulation device can cooperate with a position determining device (e.g., optical system, near field communication system, etc.) that detects and stores the position of the electrical stimulation device in association with proper impedance characteristics along the stimulation path(s) and tracks the relative position between the electrical stimulation device and the position determining position during stimulation. Then, if the position changes, the controller can be configured to guide readjustment of the electrical stimulation device's position, according to the position determining device, until the correct position is reachieved. Alternatively, the electrical stimulation device can be configured to deliver additional electrolyte solution (e.g., saline), to or through the electrodes in an attempt to reduce impedance along the stimulation path(s). However, other variations of the method 100 can additionally or alternatively include any other suitable blocks or steps, rearrange blocks, or omit portions of blocks.

In one example of an optical position determining system, one or more cameras on the controller 220 can be used used to capture images or video of the electrical stimulation device located on or near the head. These images or video can include fiducial points located on the electrical stimulation device, such as circular features, dots, joints, angles, colored patches, and/or other features amenable to identification using techniques known in the art of computer vision. These images or video can also include identifiable points on the head, such as eyes, nose, ears, vertex, inion, preauricular point, and/or others, amenable to identification using techniques known in the art of computer vision and facial recognition. The controller 220 can create an internal virtual model of actual head and electrical stimulation device positions, and calculate an optimal position for the electrical stimulation device based on intended use, intended placement, or information specific to that user and/or informed by functional neurophysiological measurements such as EMG potentials triggered by transcranial magnetic stimulation (TMS). The controller 220 can use this model of actual position and optimal position to guide the user in readjustment of the electrical stimulation device's position.

As a person skilled in the field of biosignals will recognize from the previous detailed description and from the figures and claims, modifications and changes can be made to the preferred embodiments of the method 100 without departing from the scope of the method 100.

2. System

Figure 6A:
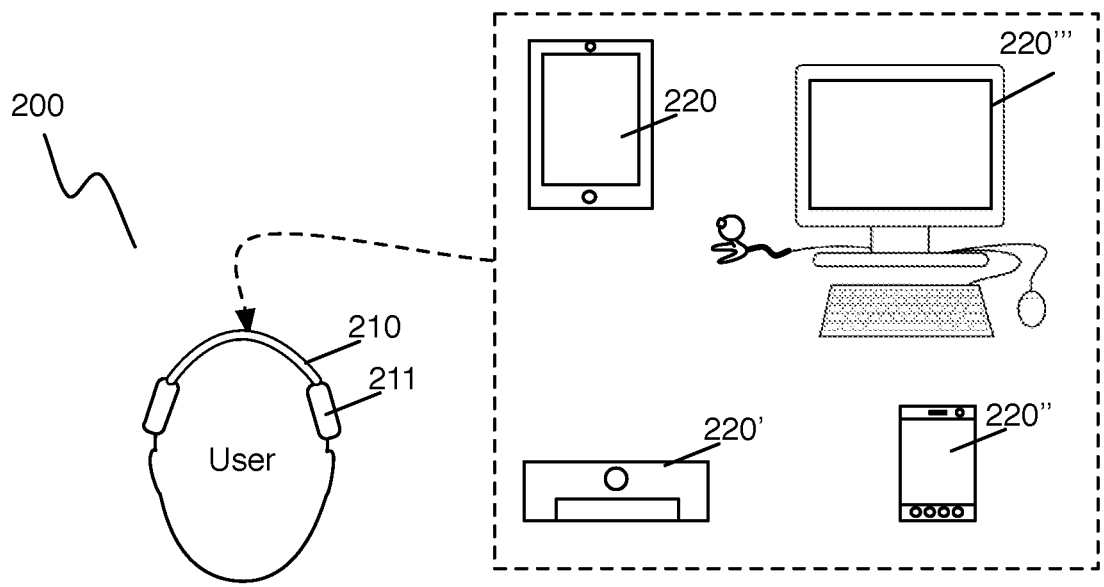
FIG. 6A depicts an embodiment of a system for improving provision of electrical stimulation.
Figure 6B:
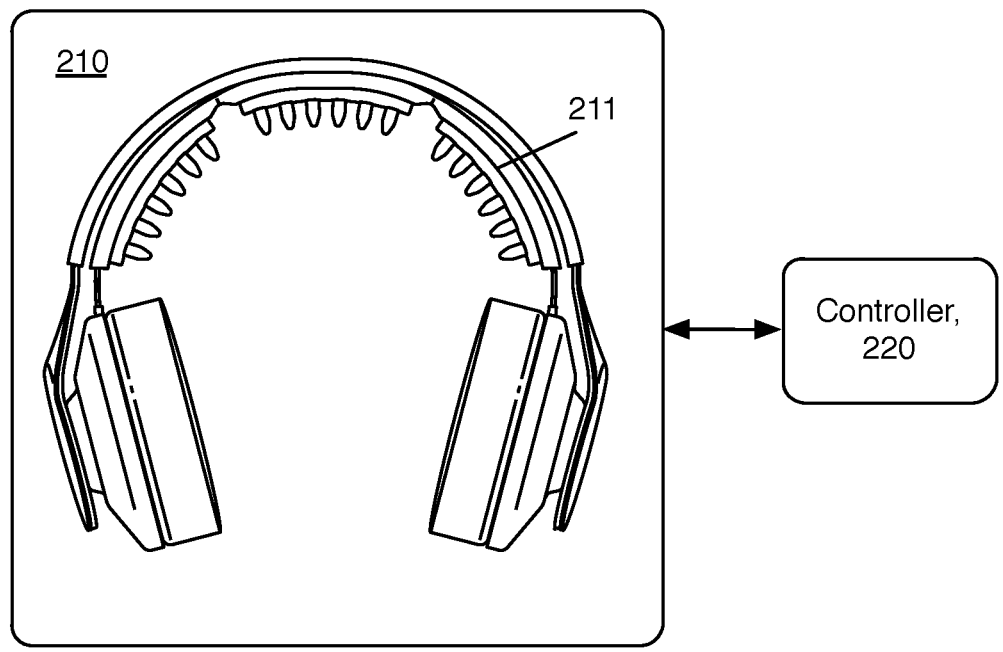
FIG. 6B depicts examples of various system components in a system for improving provision of electrical stimulation.

As shown in FIGS. 6A and 6B, an embodiment of a system 200 for providing electrical stimulation to a user can include one or more of: an electrical stimulation device 210 configured to provide a stimulation session to the user and monitor impedance characteristics along stimulation path(s) associated with the stimulation session; and a controller 220 coupled to the electrical stimulation device, wherein the controller is configured to control provision and modulation of the stimulation session to the user according to a waveform definition and the monitored impedance characteristics. The system 200 is preferably configured to perform an embodiment of the method 100 described above, but can additionally or alternatively be configured to perform any other suitable method, including methods described in one or more of: U.S. application Ser. No. 14/470,683 titled "Electrode System for Electrical Stimulation" and filed on 27, Aug. 2014, U.S. application Ser. No. 14/470,747 titled "Method and System for Providing Electrical Stimulation to a User"; U.S. App. No. 62/292,511 titled "Stimulation System and Method" and filed on 8, Feb. 2016; U.S. App. No. 62/442,350 titled "Stimulation System and Method" and filed on 4, Jan. 2017; U.S. application Ser. No. 14/878,647 titled "Electrode System for Electrical Stimulation" and filed on 8, Oct. 2015; U.S. application Ser. No. 15/059,095 titled "Method and System for Providing Electrical Stimulation to a User" and filed on2, Mar. 2016; and U.S. application Ser. No. 15/335,240 titled "Electrode Positioning System and Method" and filed on 26, Oct. 2016.

The system 200 preferably includes embodiments, variations, and examples of system elements as described in U.S. App. No. 62/292,511 filed 8, Feb. 2016 and titled "Stimulation System and Method" and U.S. Provisional Application Ser. No. 62/442,350 filed 4, Jan. 2017 and titled "Stimulation System and Method", which are each incorporated herein in their entireties by this reference. The system 200 can additionally or alternatively include elements described in one or more of: U.S. application Ser. No. 14/470,683 titled "Electrode System for Electrical Stimulation" and filed on 27, Aug. 2014, U.S. application Ser. No. 14/470,747 titled "Method and System for Providing Electrical Stimulation to a User"; U.S. App. No. 62/292,511 titled "Stimulation System and Method" and filed on 8, Feb. 2016; U.S. App. No. 62/442,350 titled "Stimulation System and Method" and filed on 4, Jan. 2017; U.S. application Ser. No. 14/878,647 titled "Electrode System for Electrical Stimulation" and filed on 8, Oct. 2015; U.S. application Ser. No. 15/059,095 titled "Method and System for Providing Electrical Stimulation to a User" and filed on 2, Mar. 2016; and U.S. application Ser. No. 15/335,240 titled "Electrode Positioning System and Method" and filed on 26, Oct. 2016.

The electrical stimulation device 210 is preferably in communication with the controller 220, and functions to deliver electrical stimulation to a user through a set of electrodes 211. The electrical stimulation device 210 is preferably configured to generate and provide TES treatments, but can additionally or alternatively be configured to provide any other suitable electrical stimulation treatment, as described in relation to the method(s) above. Preferably, the electrical stimulation device 210 comprises an electrode array 221, but can alternatively comprise a single electrode. The controller 220 is operable to output a current value based upon the set current output according to the waveform definition, wherein the output value is set from a computing system (e.g., central processing unit, microcontroller, etc.).

Figure 7A:
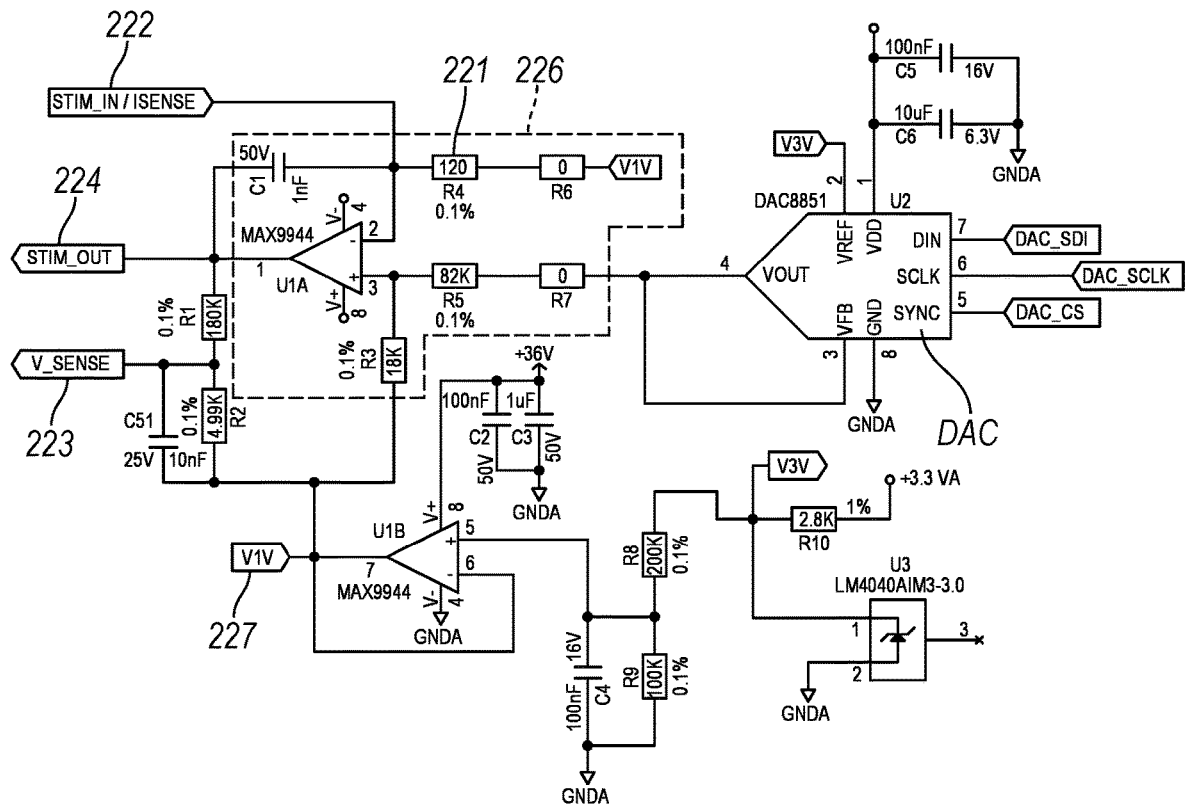
FIGS. 7A-7B depict example electronics diagrams associated with a system for improving provision of electrical stimulation.
Figure 7B:
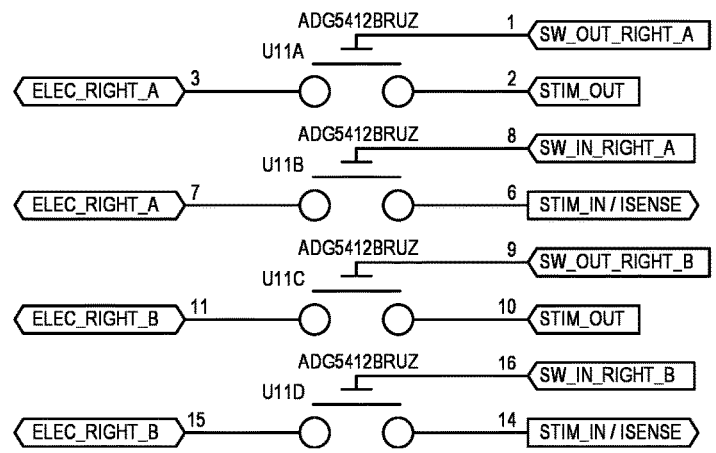

In an example, as shown in FIGS. 7A and 7B, and in relation to impedance measurements, the electrical stimulation device 210 and the controller 220 can include an electronics configuration that supports one or more of the following: a current limiting resistor 221 that limits the output current regardless of any faults or errors in software/the system, wherein the value of the current limiting resistor determines the maximum allowable current output; a first node 222 at which voltage can be measured in order to sense current through the stimulation path (e.g., from STIM_OUT to STIM_IN/ISENSE, with a minimum 14 bits of resolution, 10 times per second), wherein the current value is used with a voltage measurement to calculate impedance; a second node 223 that is used to measure voltage (e.g., with a minimum 14 bits of resolution, 10 times a second), wherein the voltage value is used with the current measurement from 222 to calculate impedance; and a voltage controlled current output 224 that can route current through a normally-open switching device (e.g., an analog switch solid state relay), in series with the electrodes to the user, an example of which is shown in FIG. 7B. In this example, the stimulation path is from STIM_OUT to STIM_IN/ISENSE; however, the stimulation path can additionally or alternatively be defined in any other suitable manner (e.g., through another ground path).

In embodiments such as the example shown in FIG. 7A, the output stage 226 can be referenced not to ground, but to a 1V reference 227, so that the output stage 226 can apply a small negative voltage across the stimulation path if necessary, without reconfiguring any multiplexer or switches after the output stage, in addition to being able to apply a normal full-scale positive voltage. The small negative voltage (in this example, <1V) can be produced by the output stage 226, when necessary, to overcome electrochemical polarization at the electrode-to-electrolyte interface. For example, if the output stage 226 is governed by the DAC to hold a constant zero current across the user's body region, but if electrode polarization has occurred (e.g., such that a non-zero current would flow if the output stage 226 were to apply zero voltage), the output stage 226 with the reference 227 can be operable to apply a small negative voltage to maintain the constant zero current.

The method 100 and system 200 of the preferred embodiment and variations thereof can be embodied and/or implemented at least in part as a machine configured to receive a computer-readable medium storing computer-readable instructions. The instructions are preferably executed by computer-executable components preferably integrated with the system 200 and one or more portions of the processor and/or a controller. The computer-readable medium can be stored in the cloud and/or on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of neuromodulation will recognize from the previous detailed description and from the figures and claims, modifications and changes can be made to the preferred embodiments of the invention without departing from the scope of this invention defined in the following claims.

We claim:

1. A method for providing electrical stimulation to a user with an electrical stimulation device in communication with a controller, the electrical stimulation device configured to be arranged at a head region of the user, the method comprising:
   upon activation of the electrical stimulation device, transitioning the electrical stimulation device from a baseline state to a first impedance monitoring state;
   during the first impedance monitoring state, determining a first impedance value of the electrical stimulation device;
   in response to determining that the first impedance value does not satisfy a first impedance criterion, guiding, with the controller, an adjustment of a position of the electrical stimulation device at the head region of the user until the first impedance criterion is satisfied, wherein guiding, with the controller, the adjustment of the position of the electrical stimulation device at the head region of the user comprises visually guiding the user, with a display of the controller, to adjust the position of a head-mountable portion of the electrical stimulation device;
   in response to determining that the first impedance value does satisfy the first impedance criterion, transitioning the electrical stimulation device from the first impedance monitoring state to a stimulation regime comprising a second monitoring state having a second criterion, wherein the stimulation regime provides an electrical stimulation session, according to a set of waveform features, to the user, wherein transitioning the electrical stimulation device to the stimulation regime comprises ramping up the stimulation regime; and
   in response to detecting that the second criterion is not satisfied, transitioning the electrical stimulation device from the stimulation regime to the first impedance monitoring state.

2. The method of claim 1, wherein guiding the adjustment of a position of the electrical stimulation device comprises guiding an adjustment of at least one of a set of electrodes of the electrical stimulation device in a direction tangential to a scalp surface of the head region.

3. The method of claim 1, wherein guiding the user with the controller comprises guiding the user with an application executing on a mobile device associated with the user and communicatively coupled to the electrical stimulation device, the mobile device comprising the controller.

4. The method of claim 3, wherein guiding the user with the controller comprises rendering, at a display of the mobile computing device, a representation of the head-mountable portion of the electrical stimulation device and a representation of a set of electrodes of the electrical stimulation device relative to the head-mountable portion.

5. The method of claim 4, wherein the set of electrodes are reversibly coupled to the head-mountable portion.

6. The method of claim 3, wherein guiding the user with the controller further comprises providing, through the application, a notification for the user to deliver a solution to the set of electrodes configured to reduce an impedance along a stimulation path.

7. The method of claim 1, wherein transitioning to the first impedance monitoring state comprises producing a set of biphasic current pulses at the electrical stimulation device.

8. The method of claim 7, wherein implementing the first impedance criterion comprises comparing impedance measurements across a subset of the set of biphasic current pulses to a threshold impedance value, and transitioning the electrical stimulation device from the first impedance monitoring state to the stimulation regime if impedance measurements are below the threshold impedance value for a predetermined duration of time.

9. The method of claim 1, wherein transitioning the electrical stimulation device from the stimulation regime to the first impedance monitoring state is performed at a first time point, wherein the method further comprises:
   in response to detecting that a third impedance criterion of the first impedance monitoring state is satisfied, transitioning the electrical stimulation device from the first impedance monitoring state to the stimulation regime at a second time point.

10. The method of claim 9, wherein implementing the first impedance monitoring state includes implementing a two-part hysteresis criterion for reducing cycling between at least one of the first impedance monitoring state, the second monitoring state, and the stimulation regime.

11. The method of claim 9, wherein the first impedance monitoring state comprises measuring impedance with the electrical stimulation device according to a first technique, and wherein the second monitoring state comprises measuring impedance with the electrical stimulation device according to a second technique that is different from the first technique.

12. The method of claim 9, wherein the first impedance criterion of the first impedance monitoring state has a first impedance value, and wherein the third impedance criterion of the first impedance monitoring state has a second impedance value greater than the first impedance value.

13. A method for providing electrical stimulation to a user with an electrical stimulation device in communication with a controller, the electrical stimulation device configured to be arranged at a head region of the user, the method comprising:
   upon activation of the electrical stimulation device, transitioning the electrical stimulation device from a baseline state to a first impedance monitoring state;
   during the first impedance monitoring state, determining a first impedance value of the electrical stimulation device;

in an event that the first impedance value does not satisfy a first impedance criterion, guiding, with the controller, a modification of a set of electrodes of the electrical stimulation device at the head region of the user until the first impedance criterion is satisfied, wherein guiding, with the controller, the modification of the electrical stimulation device at the head region of the user comprises visually guiding the user with a display of the controller; and in response to detecting satisfaction of the first impedance criterion, transitioning the electrical stimulation device from the first impedance monitoring state to a stimulation regime comprising a second monitoring state having a second criterion, wherein the stimulation regime provides an electrical stimulation session, according to a set of waveform features, to the user, wherein transitioning the electrical stimulation device to the stimulation regime comprises ramping up the stimulation regime; and in response to detecting that the second criterion is not satisfied, transitioning the electrical stimulation device from the stimulation regime to the first impedance monitoring state.

14. The method of claim 13, wherein guiding, with the controller, a modification of the set of electrodes comprises guiding the user, with a display of the controller, an adjustment of a position of at least one of the set of electrodes the electrical stimulation device at the head region of the user until the first impedance criterion is satisfied.

15. The method of claim 13, wherein guiding the user with the controller comprises providing, through the application, a notification for the user to deliver a solution to the set of electrodes configured to reduce an impedance along a stimulation path.

16. The method of claim 13, wherein transitioning the electrical stimulation device form the stimulation regime to the first impedance monitoring state is performed at a first time point, wherein the method further comprises:

in response to detecting that a third impedance criterion of the first impedance monitoring state is satisfied, transitioning the electrical stimulation device from the first impedance monitoring state to the stimulation regime at a second time point.

17. The method of claim 16, wherein implementing the first impedance monitoring state includes implementing a two-part hysteresis criterion for reducing cycling between at least one of the first impedance monitoring state, the second monitoring state, and the stimulation regime.

18. The method of claim 16, wherein the first impedance criterion of the first impedance monitoring state has a first impedance value, and wherein the third impedance criterion of the first impedance monitoring state has a second impedance value greater than the first impedance value.

19. The method of claim 13, wherein transitioning to the first impedance monitoring state comprises producing a set of biphasic current pulses at the electrical stimulation device.

20. The method of claim 19, wherein implementing the first impedance criterion comprises comparing impedance measurements across a subset of the set of biphasic current pulses to a threshold impedance value, and transitioning the electrical stimulation device from the first impedance monitoring state to the stimulation regime if impedance measurements are below the threshold impedance value for a predetermined duration of time.

* * * * *